United States Patent
Cecchi

(10) Patent No.: US 6,596,886 B1
(45) Date of Patent: Jul. 22, 2003

(54) METHOD FOR PRODUCING A NON-FATTY SOFTENER BASED ON WAX-ESTERS

(75) Inventor: Georges Cecchi, Marseille (FR)

(73) Assignee: Sophim, Peyrius (FR)

( * ) Notice: Subject to any disclaimer, the term of this patent is extended or adjusted under 35 U.S.C. 154(b) by 553 days.

(21) Appl. No.: 10/048,977

(22) PCT Filed: Jul. 4, 2000

(86) PCT No.: PCT/FR00/01901

§ 371 (c)(1),
(2), (4) Date: Feb. 15, 2002

(87) PCT Pub. No.: WO02/02498

PCT Pub. Date: Jan. 10, 2002

(51) Int. Cl.⁷ .................................................. C11C 3/10
(52) U.S. Cl. ...................... 554/167; 554/169; 554/227; 424/401
(58) Field of Search ................................ 554/167, 169, 554/227; 424/401

(56) References Cited

U.S. PATENT DOCUMENTS 5,399,731 A    3/1995  Wimmer

FOREIGN PATENT DOCUMENTS

| JP | 06/345617 | 12/1994 |
|---|---|---|
| WO | 90/15127 | 12/1990 |

*Primary Examiner*—Deborah D. Carr
(74) *Attorney, Agent, or Firm*—Dennison, Schultz & Dougherty

(57) ABSTRACT

The invention relates to a process for manufacturing non-oily emollients with a molecular weight below about 600 Dalton, preferably below 550 Dalton, and still more preferably below about 450 Dalton, based on alcohol and fatty acid esters (wax-esters), which consists of the following steps:

a) interesterification of the triglycerides contained in a fatty material by a primary alcohol, in the presence of a catalyst;

b) elimination of the catalyst;

c) distillation of the residual alcohol preferably in the presence of a bleaching agent followed by elimination of the bleaching agent;

d1) either frigelisation of the preferably bleached residue such that residual glycerides are at least partially crystallized, followed by elimination of said crystallized residual glycerides, d2) or hydrogenation of the residue, preferably bleached.

19 Claims, No Drawings

METHOD FOR PRODUCING A NON-FATTY SOFTENER BASED ON WAX-ESTERS

The invention relates to the field of fine chemicals. More precisely, the invention relates to a process for the manufacture of a non-oily emollient.

Emollients are widely used in the cosmetic and pharmaceutical industries to render dry skin soft and to improve its elasticity. The term emollient generally refers to the set of perceptions conveyed by the senses of touch and sight. Perceptions evoked by touch are softness, elasticity and smoothness. Perceptions evoked by sight are shininess and dullness.

A considerable number of emollients are offered by suppliers of cosmetic starting materials. These emollients differ from each other in terms of their chemistry, as well as in terms of the result of two factors: emollience on application and residual emollience. There are therefore emollients with a protective effect, others with a highly oily effect, while some give the impression of dryness and others still have an astringent effect.

The vast majority of emollients are characterised by the presence of fatty acids with fairly long carbon chains, either linear or branched. These fatty acids are themselves combined, in the form of esters, with alcohols with more or less long carbon chains which are also linear or branched. It is these esters and fatty acids which constitute the basis of the emollient effect. Generally, two groups of esters are considered to make up this category of emollient: those of a completely natural origin and those of synthetic origin, synthesis meaning esterification of the fatty acid by an alcohol. Synthetic esters are usually manufactured from saturated fatty acids. This confers great stability on them with regard to oxidation but eliminates the possibility of their being involved in any biosynthetic processes in the epidermis. It is well-established that polyunsaturated fatty acids (linoleic and linolenic acid), called essential fatty acids, can be transformed by the enzymes of the epidermis into other polyunsaturated fatty acids which, amongst other effects, are likely to limit the loss of transepidermal moisture. This limiting effect on loss of moisture provides skin emollience and it is this emollient effect that is sought after in esters of natural origin, such as those found in plant oils and fats, marine oils and some animal fatty materials.

All these fatty materials consist of a mixture of esters that are triglycerides or triesters of glycerol and fatty acids. It is the properties of the fatty acids found in these esters which give the resultant fatty material its consistency. Therefore the richer these fatty materials are in saturated fatty acids, the greater their consistency to the point where fairly solid fats or butters are obtained at 20° C. Totally solid products can actually be obtained at this temperature with completely hydrogenated fats. Conversely, the lower the content in unsaturated fatty acids (mono- or poly-), the more likely the fat is to be totally fluid at 20° C.

This is true of vegetable oils which are characterised by a composition in which overall content in unsaturated fatty acids is often greater than 85%. The liquid consistency of oils is one advantage in terms of an emollient effect. To this fluid consistency is added the effect of essential fatty acids such as linoleic acid, always present in vegetable oils in varying proportions as a function of the botanical origin of oleaginous species from which they originate. As mentioned earlier, transformation of linoleic acid into other unsaturated fatty acids via a biosynthetic process leads to a significant moisturizing effect which contributes to maintaining the epidermis in a good state of emollience. Finally, the important biological role played by the unsaponifiable compounds present, such as squalene, carotene, triterpenic alcohols and phytosterols, have to be taken into consideration with vegetable oils. These oils can, however, be completely hydrogenated to give emollient fatty materials, devoid of biological activity but oxidatively very stable, and which have the required consistency for some creams.

While all these advantages are well known, vegetable oils and fatty materials in general nonetheless have the serious disadvantage of being oily to the touch after application to the skin because of their low rate of skin penetration. Generally speaking, the rate of percutaneous penetration of a molecule is inversely proportional to its molecular weight. This rate is relatively high for a molecular weight of 400 Dalton but above this molecular weight, the rate of penetration decreases considerably. However, the molecular weight of triglycerides in vegetable oils is around 870 Dalton, much higher than the limit of 400 Dalton. It is therefore clear that vegetable oils, such as those used in cosmetic and pharmaceutical formulations, can give the impression of being oily as a result of triglycerides which only penetrate the skin very slowly.

The problem faced is therefore to find a process for manufacturing emollients where the molecular weight of the principal compounds is below about 600, preferably around 500, and still more preferably below about 450 Dalton, in order to obtain vegetable oil and fatty materials based emollient preparations that are not oily to the touch. The second objective consists in transforming vegetable oils or fatty materials in general and purifying the product obtained under conditions such that the intactness of their fatty acids and insaponifiable matter is not lost so that all the properties of fatty materials can be exploited without the inconvenience of their being oily.

This problem is resolved by the process of the invention which is comprised of the following steps:

a) interesterification of the triglycerides contained in a fatty material, preferably of vegetable origin, by a primary alcohol, preferably of plant origin, in the presence of a catalyst;

b) elimination of the catalyst;

c) distillation of the residual alcohol, preferably in the presence of a bleaching agent, followed by elimination of the bleaching agent;

d1) either frigelisation of the preferably bleached residue such that residual glycerides are at least partially crystallized, followed by elimination, especially by filtration, of said crystallized residual glycerides;

d2) or hydrogenation of the residue, preferably bleached.

In step d1), said residual glycerides are mono-, di- or triglycerides resulting from esterification by said primary alcohol in step a). Their elimination results in products that are completely liquid at the frigelisation temperature, notably at room temperature, preferably at a temperature of at least 15° C.

In step d2), hydrogenation of the residue leads to the formation of products with higher melting points at room temperature, generally melting points between a temperature of 25° C. and 80° C., depending on the molecular weight of the products.

In the sense of this invention, "fatty material" refers to a refined or crude vegetable oil or fat, possibly hydrogenated, a refined or crude marine oil, possibly hydrogenated, or a refined or crude animal fat, possibly hydrogenated, or a refined or crude anhydrous dairy fat, possibly hydrogenated.

The alcohol use in the interesterification step can be chosen from the $C_1$–$C_{22}$ alcanols, $C_3$–$C_{22}$ alcenols or $C_3$–$C_{22}$ branched alcohols. These branched alcohols are alcohols likely to carry $C_1$–$C_8$ alkyl substituents. Among the $C_1$–$C_{22}$ alcanols, $C_4$–$C_{18}$ alcanols are preferred, particularly $C_6$–$C_{18}$ alcanols. Among the $C_3$–$C_{22}$ branched alcohols, $C_8$–$C_{22}$ alcohols are preferred. The fatty acid esters obtained from $C_1$–$C_{22}$ branched primary alcohols, preferably $C_6$ to $C_{18}$, are called wax-esters in this invention. The term wax-esters generally covers esters of fatty acids and fatty alcohols that are solid at room temperature. By extension, the term is also used to cover any fatty acid or fatty alcohol esters that are solid or liquid at room temperature obtained in accordance with this invention. By varying the length of the saturated alcohol used, it is possible to obtain wax-esters from vegetable oils that are liquid at 20° C.

According to a preferred embodiment of the invention, the alcohol is chosen from among 1-hexanol, 1-octanol, 1-decanol, 1-dodecanol, 1-tetradecanol, 1-hexadecanol, 1-octadecanol, hexyldecanol or oleic alcohol.

Advantageously, about 30% to about 150% by weight of alcohol with respect to fatty material weight is used in step a). At the end of the interesterification reaction, content in residual alcohol is generally between about 20% by weight and about 35% by weight with respect to the weight of starting alcohol used.

The catalyst used to trigger the interesterification reaction is preferably an alkaline base, an alkaline metal alcoholate, an alkaline metal or a strong acid.

Advantageously, the catalyst is chosen from among soda, sodium methylate, metallic sodium or 4-toluene sulphonic acid.

The interesterification reaction is generally carried out for about 0.5 hour to about 10 hours, with stirring under an inert atmosphere, for example nitrogen, and at a temperature at least equal to about 100° C. and at most equal to about 200° C.

Advantageously, elimination of the catalyst in step b), when the catalyst is of the alkaline type, is carried out with an excess of about 500%, with respect to the stoichiometric amount, of a strong acid such as sulphuric acid or hydrochloric acid in aqueous solution of at least N and at most 5N, necessary for neutralisation of the alkaline catalyst, by stirring at room temperature for at least 30 minutes and at most about 1 hour. The catalyst neutralisation process is followed by washing with water, with each washing carried out under stirring at a temperature between about 80° C. and about 100° C., using an amount of water equal to at least 10% by weight and at most 20% by weight of the product weight to be washed. Between two and four washes are generally needed to attain neutrality. When the catalyst is a strong acid, elimination of this acid is advantageously carried out by straightforward washing with water. To carry out these washing processes at room temperature between about 80° C. and about 100° C. with stirring, an amount of water is used equal to at least 10% by weight and at most 20% by weight of product weight to be washed. As many washes as necessary are carried out until the washing water has a neutral pH.

Distillation of the residual alcohol in the product neutralised in step c) is carried out under absolute pressure of about 10 to 100 Pascal, at a temperature equal to at least 65° C. and at most about 230° C., for a period of time generally equal, at most, to about 4 hours and preferably equal to about 2 hours. Advantageously, said distillation process is carried out in the presence of a quantity of bleaching agent, for example activated charcoal, equal to at least about 0.1% by weight and at most about 1% by weight of the product to be distilled. After cooling down completely, the bleaching agent is generally separated from the distillation residue by straightforward filtration.

The frigelisation process is carried out in step d1) by stirring the bleached distillate at a temperature between about 10° C. and about 14° C. for a period of time generally at least equal to about 1 hour and at most to about 4 hours after which the frigelised product is filtered.

The frigelisation temperature can be reduced but this carries a risk in that part of the wax-esters according to the invention might be crystallized and eliminated with the crystallized residual glycerides.

According to one embodiment of the invention, the product (residue) recovered after distillation of the residual alcohol is hydrogenated in a reactor under hydrogen pressure of about 1 to about 20 bar, in the presence of a catalyst such as a nickel- or palladium-based catalyst, at a temperature equal to at least 100° C. and at most about 220° C., for a period of time equal to at least about 2 hours and at most about 8 hours. Under these conditions, all unsaturated parts of the acid and alcohol carbon chain (if it is unsaturated) are hydrogenated with the hydrogenated product having an iodine number of less than 1. The catalyst is separated by straightforward filtration on paper.

Advantageously, the product obtained in step d1) or d2) has a wax-ester content (expressed as a percentage with respect to the weight of product obtained) between about 55% by weight and about 95% by weight, preferably between about 66% and about 90% by weight, and more especially between 70% by weight and about 80% by weight.

According to another aspect, the invention relates to a wax-ester based non-oily emollient which can be obtained by the process described above. This emollient has the following characteristics:

liquid, solid or fat-like consistency at 20° C., perfectly suitable for the epidermis, dry and silky to the touch, easy to spread, penetrates the epidermis quickly has dermatological properties identical to those of the starting oil.

Preferably, the non-oily emollient according to the invention consists of a mixture of:

66 to 95% by weight of wax-esters, 0.1 to 12% by weight of triglycerides, 3 to 20% by weight of diglycerides, and 1.5 to 10% by weight of monoglycerides (as proportions of these four components total 100%, to the nearest insaponifiable matter, the latter generally represents about 0.1 to 1.5% by weight).

The invention will be better understood from the following examples, given for the purpose of illustration only.

EXAMPLE 1

541 g of refined olive oil are placed in a necked flask. 459 g of oleic alcohol and 0.41 g of 50% aqueous soda are added. After creating a vacuum (5000 absolute Pa) in the flask, the flask is heated to 180° C. and the contents are stirred to homogenize the reaction medium. Once this temperature is reached, the vacuum is cut off and the atmosphere surrounding the reaction medium is pressurized with nitrogen. The flask is reacted for 6 hours at 180° C. after which it is cooled.

EXAMPLE 2

709 g of refined almond oil are placed in a necked flask. 291 g of 1-octanol and 1.4 g of sodium methylate are added.

After creating a vacuum of 5000 absolute Pa, the temperature is increased to 100° C. Once this temperature is reached, the vacuum is cut off and the flask's atmosphere is pressurized slightly with nitrogen. The temperature of the flask is then increased to 170° C. and maintained at this temperature for 6 hours. The flask is then cooled down to room temperature.

EXAMPLE 3

670 g of refined olive oil are placed in a necked flask. 330 g of 1-decanol in which 0.5 g of sodium is dissolved are added. After creating a vacuum of 5000 absolute Pa, the temperature is increased to 125° C. Once this temperature is reached, the flask's atmosphere is pressurized slightly with nitrogen. After 30 minutes of stirring at 125° C., the interesterification reaction reaches the desired level.

EXAMPLE 4

670 g of refined sunflower oil are placed in a necked flask. 330 g of 1-decanol and 1.5 g of 4-toluene sulphonic acid are added. After creating a vacuum of 5000 absolute Pa, the temperature is increased to 150° C. Once this temperature is reached, the flask's atmosphere is pressurized slightly with nitrogen. After 6 hours of stirring, the interesterification reaction reaches the desired level.

EXAMPLE 5

756 g of refined salmon oil are placed in a necked flask. 244 g of hexanol in which 0.5 g of sodium is dissolved are added. After creating a vacuum of 5000 absolute Pa, the temperature is increased to 125° C. Once this temperature is reached, the flask's atmosphere is pressurized slightly with nitrogen. After 30 minutes of stirring, the interesterification reaction reaches the desired level.

EXAMPLE 6

496 g of melted fat butter are placed in a necked flask. 504 g of oleic alcohol and 0.45 g of 50% aqueous soda are added. After creating a vacuum of 5000 absolute Pa in the flask, the flask is heated to 180° C. and the contents are stirred to homogenize the reaction medium. Once this temperature is reached, the vacuum is cut off and the atmosphere surrounding the reaction medium is pressurized with nitrogen. The flask is reacted for 6.5 hours at 180° C. after which it is cooled.

EXAMPLE 7

541 g of refined melted shea butter are placed in a necked flask. 459 g of hexyl-decanol and 1 g of sodium methylate are added. After creating a vacuum of 5000 absolute Pa, the temperature is increased to 170° C. Once this temperature is reached, the vacuum is cut off and the flask's atmosphere is pressurized slightly with nitrogen. After 7 hours, the reaction is stopped.

EXAMPLE 8

670 g of completely hydrogenated refined rapeseed oil are placed in a necked flask. 330 g of 1-decanol in which 0.5 g of sodium is dissolved are added. After creating a vacuum of 5000 absolute Pa, the temperature is increased to 125° C. Once this temperature is reached, the flask's atmosphere is pressurized slightly with nitrogen. After 30 minutes of stirring at 125° C., the interesterification reaction reaches the desired level.

EXAMPLE 9

700 g of Macadamia oil are placed in a necked flask. 300 g of 1-octanol in which 0.55 g of sodium is dissolved are added. After creating a vacuum of 5000 absolute Pa, the temperature is increased to 100° C. Once this temperature is reached, the vacuum is cut off and the flask's atmosphere is pressurized slightly with nitrogen. The temperature of the flask is then increased to 125° C. and maintained at this temperature for 45 minutes. The flask is then cooled down to room temperature.

EXAMPLE 10

670 g of refined hazelnut oil are placed in a necked flask. 330 g of 1-decanol in which 0.5 g of sodium is dissolved are added. After creating a vacuum of 5000 absolute Pa, the temperature is increased to 125° C. Once this temperature is reached, the flask's atmosphere is pressurized slightly with nitrogen. After 30 minutes of stirring at 125° C., the interesterification reaction reaches the desired level.

EXAMPLE 11

541 g of refined olive oil are placed in a necked flask. 456 g of 1-octadecanol in which 0.71 g of sodium is dissolved are added. After creating a vacuum of 5000 absolute Pa in the flask, the flask is heated to 125° C. and the contents are stirred to homogenize the reaction medium. Once this temperature is reached, the vacuum is cut off and the atmosphere surrounding the reaction medium is pressurized with nitrogen. The flask is reacted for 6 hours at 180° C. after which it is cooled.

EXAMPLE 12

The product obtained in example 3 undergoes the following treatment. With the product kept under vacuum in the reaction flask, 50 ml of 2N sulphuric acid aqueous solution are added. The temperature is increased to 90° C. and the mixture is stirred for 15 minutes then left to decant. The aqueous acid phase is drawn off, 100 ml of water are added, the mixture is stirred for 10 minutes then left to decant. This washing with water is repeated twice until neutrality is attained. The product is left to decant completely and then dried thoroughly under reduced pressure at 95° C. 960 g of the product are recovered to which activated charcoal is then added. The mixture is distilled under vacuum (70 Pa) and under nitrogen microbubbles, gradually heating the flask such that the temperature reached by the fluid at the end of distillation does not exceed 180° C. The vacuum during the distillation process is around 60 Pa. Distillation is stopped after 3 hours. 900 g of product are recovered from the distillation flask and filtered on paper to separate out the activated charcoal. 880 g of a liquid yellow product with slight precipitation are obtained. 875 g of this product are placed in a cylindrical reactor fitted with a double external coat for the coolant to pass through. The liquid is gradually cooled to a temperature of 14.5° C. by passage of the coolant, itself at 14° C. in the double coat of said frigelisation reactor, stirred for 4 hours then filtered. 850 g of a yellow liquid without a marked odour and totally liquid at 15° C. are obtained.

The product obtained after frigelisation and filtration contains (per 100 grams of product obtained):

82.2 grams of wax-ester of which
    60.9 g of 1-decyl octadecene 9c oate (decyl oleate), MW=422 dalton,
    10.2 g of 1-decyl hexadecanoate (decyl palmitate), 1.8 g of 1-decyl hexadecene 9c oate (decyl palmitoleate),
2.0 g of 1-decyl octadecanoate 9c10c oate (decyl stearate),
6.4 g of 1-decyl octadecadiene 9c10c oate (decyl linoleate),
0.5 g of 1-decyl octadecatriene 9c10c12c oate (a decyl linolenate),
0.1 g of decyl eicosanoate (decyl arachidate),
0.3 g of decyl eicosene 11c oate (decyl gadeolate),
5.5 grams of olive triglycerides,
6.0 grams of olive diglycerides,
4.0 grams of olive monoglycerides.

EXAMPLE 13

The product obtained in example 12 prior to frigelisation is hydrogenated in a stirred reactor with 1% of a nickel-based catalyst deposited on silica (25% nickel in the catalyst), under pressure of 10 bar of hydrogen at 200° C. for 6 hours. After filtration of the catalyst, a beige-white product is obtained with a melting point of 40° C. and an iodine number of less than 1.

The product obtained after hydrogenation and filtration contains (per 100 grams of product obtained):
82.2 grams of wax-ester of which
  69.7 g of 1-decyl octadecanoate (decyl stearate), MW=424 Dalton,
  11.9 g of 1-decyl hexadecanoate (decyl palmitate),
  0.4 g of decyl eicosanoate (decyl arachidate),
5.5 grams of triglycerides (palmitic 14.5%, stearic 85.0%, arachidic 0.5%),
6.1 grams of diglycerides (palmitic 14.5%, stearic 85.0%, arachidic 0.5%),
4.1 grams of monoglycerides (palmitic 14.5%, stearic 85.0%, arachidic 0.5%).

EXAMPLE 14

The product obtained in example 11 undergoes the same treatment to eliminate the catalyst by washing in 2N sulphuric acid as the product in example 12. After eliminating the washing water, 0.25% by weight of activated charcoal is added to the product obtained. The product is then distilled at 230° C. under a vacuum of 50 Pa for 2 hours. After cooling down to 60° C., the product is filtered on paper at this temperature to eliminate the bleaching agent. The filtrate is then hydrogenated under the same conditions as in example 13. After filtration of the catalyst, a product with a melting point of 57° C. and an iodine number of less than 1 is obtained.

The product obtained after hydrogenation and filtration contains (per 100 grams of product obtained):
78.0 grams of wax-ester of which
  66.3 g of 1-octadecyl octadecanoate (decyl stearate), MW=536 Dalton,
  11.3 g of 1-octadecyl hexadecanoate (decyl palmitate),
  0.4 g of 1-octadecyl eicosanoate (decyl arachidate),
6.9 grams of triglycerides (palmitic 14.5%, stearic 85.0%, arachidic 0.5%),
5.0 grams of diglycerides (palmitic 14.5%, stearic 85.0%, arachidic 0.5%),
7.6 grams of monoglycerides (palmitic 14.5%, stearic 85.0%, arachidic 0.5%).

EXAMPLE 15

750 g of olive oil are placed in a necked flask. 242 g of hexanol in which 0.5 g of sodium is dissolved are added. After creating a vacuum of 10000 absolute Pa, the temperature is increased to 100° C. Once this temperature is reached, the vacuum is cut off and the flask's atmosphere is pressurized slightly with nitrogen. The temperature of the flask is then increased to 125° C. and maintained at this temperature for 30 minutes. The flask is then cooled down to room temperature. The product obtained undergoes the same treatment to eliminate the catalyst by washing in 2N sulphuric acid as the product in example 12. After eliminating the washing water, 0.25% by weight of activated charcoal is added to the product obtained. The product is then distilled at 180° C. under a vacuum of 60 Pa for 2 hours. After cooling down, the product is filtered on paper. The filtrate obtained is then hydrogenated under the same conditions as in example 13. After filtration of the catalyst, a product with a melting point of 25.0° C. and an iodine number of less than 1 is obtained.

The product obtained after hydrogenation and filtration contains (per 100 grams of product obtained):
89.1 grams of wax-ester of which
  74.9 g of 1-hexyl octadecanoate (hexyl stearate), MW=368 Dalton,
  13.1 g of 1-hexyl hexadecanoate (hexyl palmitate),
  1.1 g of 1-hexyl eicosanoate (hexyl arachidate),
1.1 grams of triglycerides (palmitic 14.5%, stearic 85.0%, arachidic 0.5%),
3.4 grams of diglycerides (palmitic 14.5%, stearic 85.0%, arachidic 0.5%),

EXAMPLE 16

600 g of olive oil are placed in a necked flask. 402 g of 1-tetradecanol in which 0.8 g of sodium is dissolved are added. After creating a vacuum of 5000 absolute Pa, the temperature is increased to 100° C. Once this temperature is reached, the vacuum is cut off and the flask's atmosphere is pressurized slightly with nitrogen. The temperature of the flask is then increased to 125° C. and maintained at this temperature for 30 minutes. The flask is then cooled down to room temperature. The product obtained undergoes the same treatment to eliminate the catalyst by washing in 2N sulphuric acid as the product in example 12. After eliminating the washing water, 0.25% by weight of activated charcoal is added to the product obtained. The product is then distilled at 200° C. under a vacuum of 60 Pa for 2 hours. After cooling down, the product is filtered on paper. The filtrate obtained is then hydrogenated under the same conditions as in example 13. After filtration of the catalyst, a product with a melting point of 48° C. and an iodine number of less than 1 is obtained.

The product obtained after hydrogenation and filtration contains (per 100 grams of product obtained):
78.9 grams of wax-ester of which
  64.0 g of 1-tetradecyl octadecanoate (tetradecyl stearate), MW=536 Dalton,
  13.6 g of 1-tetradecyl hexadecanoate (tetradecyl palmitate),
  1.3 g of 1-tetradecyl eicosanoate (tetradecyl arachidate),
8.8 grams of triglycerides (palmitic 14.5%, stearic 85.0%, arachidic 0.5%),
5.3 grams of diglycerides (palmitic 14.5%, stearic 85.0%, arachidic 0.5%),
3.9 grams of monoglycerides (palmitic 14.5%, stearic 85.0%, arachidic 0.5%).

What is claimed is:

1. Process for the manufacture of a non-oily emollient with a molecular weight below about 600 Dalton, based on alcohol and fatty acid wax esters, comprising the steps of:
   a) interesterifying triglycerides contained in a fatty material by a primary alcohol, in the presence of a catalyst;
   b) eliminating the catalyst;
   c) distilling residual alcohol;
   d1) either chilling the residue such that residual glycerides are at least partially crystallized, followed by eliminating said crystallized residual glycerides, or
   d2) hydrogenating the residue.

2. Process according to claim 1 wherein the alcohol in step a) is a $C_1$–$C_{22}$ alkanol, $C_3$–$C_{22}$ alkenol or $C_3$–$C_{22}$ branched alcohol.

3. Process according to claim 2 wherein said alcohol is selected from the group consisting of 1-hexanol, 1-octanol, 1-decanol, 1-dodecanol, 1-tetradecanol, 1-hexadecanol, loctadecanol, hexyldecanol and oleic alcohol.

4. Process according to claim 2 wherein the alcohol is used in an amount between about 30% by weight and about 150% by weight with respect to fatty material weight.

5. Process according to claim 1 wherein the catalyst in step a) is selected from the group consisting of an alkaline base, an alkaline metal alcoholate, an alkaline metal and a strong acid.

6. Process according to claim 5 wherein the catalyst is selected from the group consisting of soda, sodium methylate, metallic sodium and 4-toluene sulphonic acid.

7. Process according to claim 1 wherein the interesterification reaction is carried out at a temperature between about 100° C. and about 200° C.

8. Process according to claim 1 wherein the residual alcohol at the end of the interesterification reaction is present in an amount of between about 20% by weight and about 35% by weight with respect to the weight of starting alcohol used.

9. Process according to claim 1 wherein the catalyst is eliminated in step b) by at least one washing with water at a temperature between about 80° C. and about 100° C., optionally preceded by treatment with a strong acid, until the washing water attains neutral pH.

10. Process according to claim 1 wherein distillation of the residual alcohol in step c) is carried out under pressure in the range of 10 to 100 Pascal and at a temperature between about 65° C. and 230° C.

11. Process according to claim 1 wherein distillation of the residual alcohol in step c) is carried out in the presence of an amount of bleaching agent between about 0.1% by weight and about 1% by weight with respect to the weight of product to be distilled.

12. Process according to claim 1 wherein chilling of the residue in step d1) is carried out at a temperature between about 10° C. and about 14° C.

13. Process according to claim 1 wherein hydrogenation of the chilled product or residue is carried out under hydrogen pressure of about 1 and about 20 bar at a temperature between about 100° C. and about 220° C.

14. Process according to claim 1 wherein the product obtained at the end of step d1) or step d2) has a fatty acid and fatty alcohol ester content between about 55% by weight and about 95% by weight.

15. Non-oily emollient based on fatty acid and fatty alcohol ester obtained by the process according to claim 1.

16. Process according to claim 1, wherein the emollient has a molecular weight below 550 Dalton.

17. Process according to claim 1, wherein the emollient has a molecular weight below 450 Dalton.

18. Process according to claim 1, wherein said distilling is carried out in the presence of a bleaching agent, followed by eliminating the bleaching agent.

19. Process according to claim 7, wherein the interesterification reaction is carried out under an inert atmosphere.

* * * * *